United States Patent
Goldstein et al.

(10) Patent No.: US 10,052,426 B2
(45) Date of Patent: Aug. 21, 2018

(54) METHODS OF ADMINISTERING NITRIC OXIDE TO ARTERIAL OR ARTERIALIZED BLOOD

(71) Applicant: Mallinckrodt Hospital Products IP Limited, Dublin (IE)

(72) Inventors: Brahm Goldstein, Chalfont, PA (US); Jim Potenziano, Binghamton, NY (US)

(73) Assignee: Mallinckrodt Pharma IP Trading D.A.C., Dublin (IE)

(*) Notice: Subject to any disclaimer, the term of this patent is extended or adjusted under 35 U.S.C. 154(b) by 24 days.

(21) Appl. No.: 14/402,786

(22) PCT Filed: May 30, 2013

(86) PCT No.: PCT/US2013/043232
§ 371 (c)(1),
(2) Date: Nov. 21, 2014

(87) PCT Pub. No.: WO2013/181322
PCT Pub. Date: Dec. 5, 2013

(65) Prior Publication Data
US 2015/0151034 A1    Jun. 4, 2015

Related U.S. Application Data

(60) Provisional application No. 61/653,499, filed on May 31, 2012, provisional application No. 61/787,865, filed on Mar. 15, 2013.

(51) Int. Cl.
*A61K 9/00* (2006.01)
*A61K 33/00* (2006.01)
*A61M 1/16* (2006.01)
*A61M 1/36* (2006.01)

(52) U.S. Cl.
CPC ......... *A61M 1/1698* (2013.01); *A61K 9/0019* (2013.01); *A61K 33/00* (2013.01); *A61M 1/3666* (2013.01); *A61M 2202/0275* (2013.01)

(58) Field of Classification Search
CPC ... A61K 9/0019; A61K 33/00; A61M 1/1698; A61M 1/3666; A61M 1/2202; A61M 1/0275
See application file for complete search history.

(56) References Cited

U.S. PATENT DOCUMENTS

| | | | |
|---|---|---|---|
| 5,957,880 A | 9/1999 | Igo et al. | |
| 7,485,324 B2* | 2/2009 | Miller | A61K 33/00 424/405 |
| 8,790,715 B2* | 7/2014 | Montgomery | A61K 33/00 128/202.26 |
| 2007/0190184 A1 | 8/2007 | Montgomery et al. | |
| 2008/0160107 A1 | 7/2008 | McCaney et al. | |

FOREIGN PATENT DOCUMENTS

JP      2001-079083      3/2001

OTHER PUBLICATIONS

Tienush Rassaf, Michael Preik, Petra Kleinbongard, Thomas Lauer, Christian Heiß, Bodo-Eckehard Strauer, Martin Feelisch and Malte Kelm, "Evidence for in vivo transport of bioactive nitric oxide in human plasma", The Journal of Clinical Investigation, 109:1241-1248 (2002).*
PCT International Preliminary Report on Patentability in PCT/US2013/043232, dated Dec. 11, 2014, 6 pages.
PCT International Search Report and Written Opinion in PCT/US2013/043232, dated Oct. 7, 2013, 10 pages.
Checchia, Paul A., et al., Nitric Oxide Delivery During Cardiopulmonary Bypass Reduces Postoperative Morbidity in Children—A Randomized Trial, *J. Thorac. Cardiovasc Surg.* vol. 146 No. 3 2013, 530-536.
Creagh-Brown, Benedict C., et al., Bench-to-bedside review: Inhaled nitric oxide therapy in adults, *Critical Care* vol. 13 No. 3 2009, 8 pages.
Giustarini, Daniela, et al., Nitric oxide and S-nitrosothiols in human blood, *Clinica Chimica Acta* vol. 330 2003, 85-98.
Lowson, Stuart M., et al., The Effect of Nitric Oxide on Platelets When Delivered to the Cardiopulmonary Bypass Circuit, *Anesth. Analg.* vol. 89 1999, 1360-65.
Sly, M. Kurt, et al., Inhibition of Surface-Induced Platelet Activation by Nitric Oxide, *ASAIO Journal* vol. 41 1995, M394-M398.
Thippeswamy, T., et al., Nitric oxide, a biological double-faced janus—Is this good or bad?, *Histol. Histopathol.* vol. 21 2006, 445-458.
Office Action in Australian Application No. 2013267418 dated Jul. 24, 2017, 5 pages.
Office Action in Australian Application No. 2013267418 dated Jan. 25, 2018, 3 pages.
Office Action in European Application No. 13729170.4 dated Nov. 23, 2017, 4 pages.
Office Action in Japanese Application 2015-515168 dated Feb. 21, 2017, 4 pages.

* cited by examiner

*Primary Examiner* — John Pak
*Assistant Examiner* — Nathan W Schlientz

(57) ABSTRACT

The present invention provides methods of administering nitric oxide (NO) to a patient, the method comprising delivering nitric oxide-containing gas directly into arterial or arterialized blood. The methods of the present invention may be used in the treatment or prevention of a variety of diseases and disorders responsive to nitric oxide, including those resulting from ischemia or hypoxia.

12 Claims, 4 Drawing Sheets

METHODS OF ADMINISTERING NITRIC OXIDE TO ARTERIAL OR ARTERIALIZED BLOOD

CROSS REFERENCE TO RELATED APPLICATIONS

This application is the U.S. National Phase entry of International Application No. PCT/US2013/043232, filed May 30, 2013, which claims priority to U.S. Provisional Application No. 61/653,499, filed May 31, 2012, and to U.S. Provisional Application No. 61/787,865, filed Mar. 15, 2013.

TECHNICAL FIELD

Embodiments of the present invention generally relate to the field of methods and devices for therapeutic delivery of nitric oxide (NO) as well as stable pharmaceutical compositions comprising nitric oxide. The invention further relates to the use of such methods and devices to treat and protect cells and animals from injury, disease, and premature death.

BACKGROUND

The action of nitric oxide (NO) is considered regulatory in maintaining normal physiological homeostasis in humans and animals, i.e., host-defense, vascular tone, neurotransmission, bronchodilatation and inhibition of platelet function (see Giustarini et al., Clinica Chimica Acta (2003) 330:85-98). NO mediates blood pressure, learning and memory, immune responses, and inflammatory responses (see Thippeswamy et al., Histol. Histopathol. (2006) 21:445-458). In addition, the actions of NO have been observed in pathological conditions such as acute respiratory distress syndrome, hypertension, pulmonary hypertension, arthritis, arteriosclerosis, cancer, diabetes, some neurodegenerative diseases and stroke (see Giustarini et al., Clinica Chimica Acta (2003) 330:85-98).

Traditionally, inhaled NO (iNO) was believed to work exclusively in the lung due to inactivation by hemoglobin (Hb). That is, reaction with oxyhemoglobin to form methemoglobin and nitrate or heme iron nitrosyl hemoblogin (Hb) would cause a loss of vasodilating properties. However it has been found that a stable derivative is formed by a reaction resulting in nitrosylation of a conserved cysteine residue of the β subunit of Hb: S-nitrosylated-Hb (SNO-Hb). This reaction is favored in the presence of oxyhaemoglobin whereas binding of NO to the heme iron is favored in the deoxygenated state. See B. C. Creagh-Brown, et al. (2009) Critical Care 13:212. In the past, remote or non-pulmonary effects of exogenously administered iNO were thought to be undesirable; however, it has recently been found that the stable derivative SNO-Hb retains vasodilatory properties and therefore could be beneficial for circulating targets.

There is clearly a need in the art for improved nitric oxide delivery, particularly systemic delivery that enables delivery of NO, via the circulatory system, to target tissues and organs outside of the pulmonary system.

SUMMARY

The present invention provides methods of administering an NO-containing gas directly to arterial or arterialized blood. These methods may be utilized for a variety of purposes and may be administered to various biological materials, including cells, tissues, organs, organisms, and animals, including humans and other mammals.

One aspect of the present invention provides a method for administering nitric oxide (NO) to a patient, the method comprising delivering an NO-containing gas directly to arterial or arterialized blood. In a specific embodiment delivery may be via a cardiopulmonary bypass (CPB) circuit, with the NO-containing gas being administered to arterialized blood after blood withdrawn from the patient has passed through the oxygenator of the CPB circuit, prior to infusion of the oxygenated (arterialized) blood into the patient.

Another aspect of the present invention provides methods for administering NO to a patient, the method comprising delivering NO-containing gas to arterialized blood in an extracorporeal membrane oxygenation (ECMO) circuit. The NO-containing gas may be administered into arterialized blood after blood has been oxygenated and $CO_2$ has been excreted out of the membrane oxygenator, including at any point after blood withdrawn from the patient has passed through the membrane oxygenator of the ECMO circuit, prior to infusion of the oxygenated (arterialized) blood into the patient. In ECMO, arterialized blood into which NO-containing gas is delivered may be returned either to the arterial or venous circulation of the patient.

Another aspect of the invention provides methods for delivery of NO-containing gas directly into arterial blood by injection, catheterization, infusion, or continuous infusion thereof into an arterial blood that is extracorporeal and then reinfusion of that blood into either an artery or vein of a patient. In particular embodiments of methods of the present invention, administering or contacting is performed by intra-arterial injection or infusion of NO-containing gas.

In certain embodiments, the NO-containing gas is administered as a bolus. Other embodiments provide that the NO-containing gas is administered continuously or in a pulsatile fashion.

In certain embodiments, the delivery concentration of NO in the NO-containing gas is in the range of about 0.1-500 ppm.

In some embodiments, the delivery concentration of NO in the NO-containing gas is in the range of 1-100 ppm.

In a particular embodiment, the delivery concentration of NO in the NO-containing gas is in the range of 2-20 ppm.

In a particular embodiment, the delivery concentration of NO in the NO-containing gas is in the range of 5-40 ppm.

In a particular embodiment, the delivery concentration of NO in the NO-containing gas is in the range of 10-30 ppm.

In a particular embodiment, the delivery concentration of NO in the NO-containing gas is the containing gas is in the range of 15-25 ppm.

In a particular embodiment, the delivery concentration of NO in the NO-containing gas is 20 ppm.

In certain embodiments, the NO-containing gas for administration may be generated locally (bed-side) for immediate delivery to a patient, for example as a component of an extracorporeal oxygenation apparatus. Local generation of NO gas for immediate delivery to a patient may be accomplished by reaction of a nitrite salt, such as sodium nitrite, and a reductant, such as ascorbic acid or maleic acid, in the presence of water, or generation of NO from room air, or other potential means. The NO gas so-produced is then delivered or introduced directly into the arterial or arterialized blood of the patient. Suitable devices for such local generation and delivery are known in the art (e.g., US 2007/0190184). In an alternative embodiment, preformed NO-containing gas is administered from a gas cylinder directly into the arterial or arterialized blood of the patient.

In a particular embodiment, the NO-containing gas is administered via a device, for example an ECMO device. The NO-containing gas may be administered within the oxygenation compartment of the device, wherein the oxygenation compartment contains two components. The first component is a first gas exchange membrane (also referred to as a membrane oxygenator) which exchanges oxygen for $CO_2$ in blood to produce arterialized blood. The second component is a second gas exchange membrane which exchanges NO for $O_2$ in the arterialized blood. The first and second components can be either structurally separate components in fluid communication or combined as one structure containing separate reaction areas within the oxygenation compartment. In either case, the second component is down-stream of the first component, as defined by the direction of blood flow in the device. Thus, NO-containing gas is administered either into the oxygenation compartment after $O_2$ has been administered into the oxygenation compartment and after $CO_2$ has been released, or NO is administered downstream of the oxygenation compartment (after blood has left the oxygenator but before it is delivered back into the patient) or both.

In a related embodiment, the present invention includes a method of treating or preventing a disease, disorder, or condition that benefits from treatment with NO comprising administering to a patient an amount of NO-containing gas effective to treat such disease, disorder, or condition, wherein the NO-containing gas is administered directly into arterial or arterialized blood. In particular embodiments, the disease, disorder or condition is a respiratory, cardiovascular, pulmonary, or blood disease or disorder, or a tumor, an infection, inflammation, shock, sepsis, or stroke, in a patient.

In a further embodiment, the present invention provides a method of preventing or reducing injury to, or enhancing survivability of, a biological material exposed to ischemic, hypoxic, or injured conditions, comprising contacting the biological material with an effective amount NO via administration of an NO-containing gas directly into arterial or arterialized blood.

In one embodiment, a biological material is contacted with the NO-containing gas via administration into arterial or arterialized blood before onset of the disease, disorder or condition that benefits therefrom. In another embodiment, the biological material is contacted with the NO-containing gas via administration into arterial or arterialized blood during occurrence of the disease, disorder or condition.

The present invention further provides systems and devices for the administration of NO-containing gas directly into arterial or arterialized blood.

DETAILED DESCRIPTION OF THE INVENTION

Figure 1:
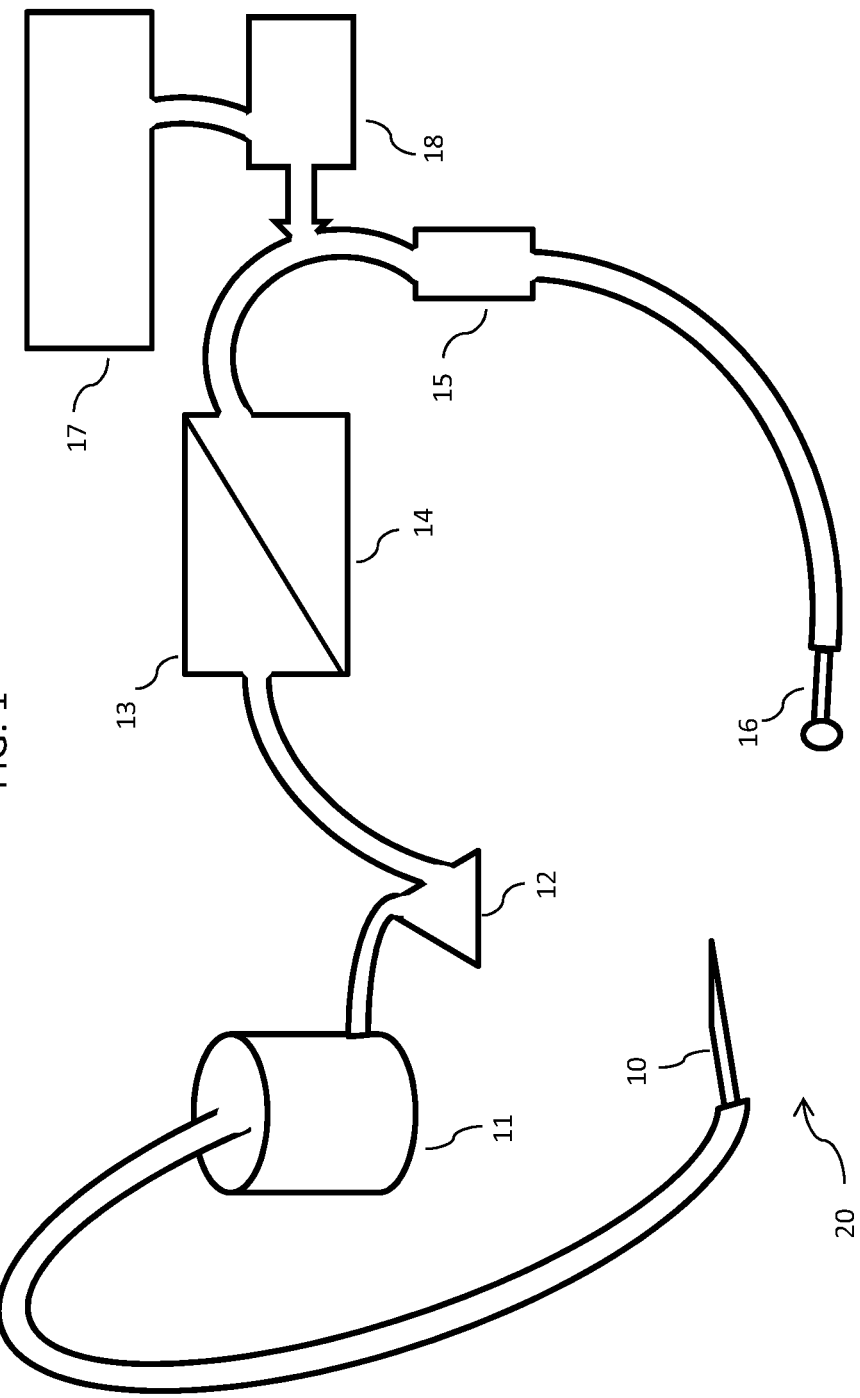
FIG. 1 illustrates a nitric oxide delivery system that can be used in accordance with one or more embodiments of the invention.

As used in the specification and appended claims, unless specified to the contrary, the following terms have the meaning indicated:

The term "arterialized blood" refers to venous blood which has been converted to arterial blood by absorption of oxygen and excretion of $CO_2$. Such conversion may be accomplished in vivo (e.g., by absorption of oxygen in the lungs) or ex vivo (e.g., by extracorporeal oxygenation).

The term "arterial blood" refers to oxygenated blood in the arterial circulation of the body.

The term "biological material" refers to any living biological material, including cells, tissues, organs, and/or organisms. It is contemplated that the methods of the present invention may be practiced on a part of an organism (such as in cells, in tissue, and/or in one or more organs), or on the whole organism. The term "in vivo biological material" refers to biological material that is in vivo, i.e., still within or attached to an organism.

"Therapeutically effective amount" refers to that amount of NO gas that, when administered via arterial or arterialized blood to a subject, preferably a human, is sufficient to effect treatment as defined herein. The amount of a compound of the invention which constitutes a "therapeutically effective amount" will vary depending on the compound, the condition and its severity, and the manner of administration, but can be determined routinely by one of ordinary skill in the art having regard to his own knowledge and to this disclosure.

"Treating" or "treatment" as used herein covers the treatment of the disease or condition of interest in a subject, preferably a human, having the disease or condition of interest, and includes: (i) preventing the disease or condition from occurring in the subject, (ii) inhibiting the disease or condition, i.e., arresting its progression; (iii) relieving the disease or condition, i.e., causing regression of the disease or condition; or (iv) relieving the symptoms resulting from the disease or condition. As used herein, the terms "disease," "disorder," and "condition" may be used interchangeably.

"Delivery concentration" refers to the concentration of NO gas in a composition of NO-containing gas for medical use which is delivered to arterial or arterialized blood. In addition to NO gas, such compositions for medical use may further comprise an inert diluent gas. It is to be understood that the delivery concentration will be diluted upon contact with blood, where it is mixed and distributed to the target biological material.

Prior to the present invention, NO was thought to react with oxyhemoglobin to form methemoglobin and nitrate or heme iron nitrosyl Hb, and thereby lose all vasodilating properties. However, it has been found that a stable derivate that retains vasodilatory properties is formed by a reaction resulting in nitrosylation of a conserved cysteine residue of the β subunit of Hb: S-nitrosylated-Hb (SNO-Hb). This reaction is favored in the presence of oxyhemoglobin whereas the prior reaction is favored in the deoxygenated state. Thus the present invention provides methods that maximize the formation of SNOHb, thereby maximizing the systemic effects of NO.

One aspect of the current invention relates to a method of delivering nitric oxide (NO) to a patient comprising administering NO-containing gas directly into arterial or arterialized blood, the administered gas having a delivery concentration of 0.01 to 10 ppm NO. In certain embodiments, the delivery concentration is in the range of 10 to 40 ppm.

According to one or more embodiments, the delivery concentration is in the range of 40 to 100 ppm. In other embodiments, the delivery concentration is greater than 100 ppm.

In one embodiment, the NO-containing gas is administered continuously, for example by continuous infusion.

In another embodiment, the NO-containing gas is delivered as a bolus rather than via a continuous administration method. A "bolus" refers to a single administration delivered over a short period of time, for example by injection from a syringe. Multiple bolus administrations may be given to the subject, each separated by a period of time.

In another embodiment, the NO-containing gas is delivered in a pulse as opposed to continuous administration. A "pulse" refers to multiple short administrations within a time period.

In an additional embodiment, a device can monitor the arterial or arterialized blood and administer the NO-containing gas at any delivery rate or concentration as necessary to provide sufficient results. Administration can automatically or manually adjust or otherwise change the flow, concentration or amount of NO during the course of delivery.

The present invention includes improved methods of systemically treating diseases and disorders with nitric oxide, which comprise administering nitric oxide gas directly into arterial or arterialized blood. Further, the present invention provides improved methods of enhancing cell survival, inducing stasis, or protecting cells or tissue from injury due to hypoxia or ischemia, which comprise administering NO-containing gas directly to arterial or arterialized blood. The invention further includes methods and devices for the preparation and administration of NO-containing gas to a subject via arterial or arterialized blood. Without wishing to be bound by any particular theory, it may be that administration of NO gas directly to oxygenated blood (e.g., after blood passes through an extracorporeal oxygenation system) or directly through an arterial catheter or intra-arterial injection will maximize the formation of SNO-Hb and thus maximize the systemic effects.

In certain embodiments, methods, compositions, and devices of the present invention are used to systemically treat or prevent any of a variety of diseases and disorders that benefit from treatment with nitric oxide. In particular embodiments, the methods of the present invention may be used to modulate biological pathways regulated or affected by nitric oxide.

Nitric oxide mediates blood pressure (causing vasodilation), learning and memory, immune responses and inflammatory responses. Accordingly, diseases, disorders or conditions potentially treatable by systemic administration of NO gas directly into arterial or arterialized blood according to the invention include respiratory, cardiovascular, pulmonary, and blood diseases, disorders or conditions, as well as hypoxemia, tumors, infections, inflammation, shock, sepsis and stroke. In specific examples, respiratory distress syndrome, asthma, bronchospastic disease, myocardial infarction, hemorrhage, sickle cell disease, platelet aggregation and major surgery may be treatable according to the methods of the invention. Further specific examples include pulmonary hypertension and hypoxemia following cardiopulmonary bypass, mitral valve replacement, heart or lung transplantation, and pulmonary embolism.

Systemic administration of nitric oxide gas into arterial or arterialized blood may be useful in suppressing, killing, and inhibiting pathogenic cells, such as tumor cells, cancer cells, or microorganisms, including but not limited to pathogenic bacteria, pathogenic mycobacteria, pathogenic parasites, and pathogenic fungi. Examples of microorganisms include those associated with a respiratory infection within the respiratory tract.

Systemic administration of nitric oxide gas into arterial or arterialized blood may enhance the survivability of biological materials, including, e.g., organs and tissues, that are subjected to ischemic or hypoxic conditions. In related embodiments, the present invention provides methods of preventing or reducing damage to biological materials, including, e.g., including cell, organ or tissue injuries resulting from ischemia or hypoxia. It is understood that a whole biological material or only a portion thereof, e.g., a particular organ, may be subjected to ischemic or hypoxic conditions.

The ischemic or hypoxic conditions may be the result of an injury or disease suffered by an organism. Examples of specific diseases that can induce ischemia or hypoxia include, but are not limited to, traumatic injury or surgery, respiratory or cardiac arrest, tumors, heart diseases, and neurological diseases. Examples of specific injuries that can result in ischemic or hypoxic conditions include, but are not limited to, external insults, such as burns, cutting wounds, amputations, gunshot wounds, or surgical trauma. In addition, injuries can also include internal insults, such as stroke or heart attack, which result in the acute reduction in circulation. Other injuries include reductions in circulation due to non-invasive stress, such as exposure to cold or radiation, or a planned reduction in circulation, e.g., during heart surgery.

In certain embodiments, methods of the present invention include systemically administering NO-containing gas directly into arterial or arterialized blood prior to development of a disease, disorder or condition treatable with NO gas, e.g., prior to an ischemic or hypoxic injury or disease insult. Examples of such situations include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient. Other examples include, but are not limited to, medical conditions in which a risk of injury or disease progression is inherent (e.g., in the context of unstable angina, following angioplasty, bleeding aneurysms, hemorrhagic strokes, following major trauma or blood loss).

In certain embodiments, methods of the present invention include systemically administering NO-containing gas directly into arterial or arterialized blood after development or onset of a disease, disorder or condition treatable with NO, e.g., after an ischemic or hypoxic injury or disease insult, or after onset any of the diseases, disorders or conditions discussed above. In a particular aspect of such embodiments, NO-containing gas may be administered to a patient suffering from the disease, disorder or condition upon recognition or diagnosis of the disease, disorder or condition.

In certain embodiments, inflammatory-related diseases or disorders may be treated by administration of NO-containing gas directly into arterial or arterialized blood. Inflammatory-related diseases or disorders which may be treatable by the methods of the present invention include, e.g., multiple sclerosis, arthritis, rheumatoid arthritis, systemic lupus erythematosus, graft versus host disease, diabetes, psoriasis, progressive systemic sclerosis, scleroderma, acute coronary syndrome, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis.

In a specific embodiment, the methods of the invention comprise administration of NO-containing gas directly into arterialized blood in an extracorporeal oxygenation system. The extracorporeal oxygenation system may be, for example, an extracorporeal membrane oxygenation system or a CPB circuit. In such methods the NO-containing gas is administered into the blood at any point in the system which is after oxygenation of the withdrawn blood. An example of CPB system 20 according to the invention is illustrated in FIG. 1. Venous blood is withdrawn from the patient through venous cannula 20, which may be inserted in the right atrium, vena cava or femoral vein. Withdrawn venous blood is collected in reservoir 11 and circulated into oxygenator 13 by pump 12, where it is oxygenated and typically cooled by heat exchanger 14 to slow the body's basal metabolism during bypass surgery. The oxygenated blood is generally filtered through filter 15 prior to return to the body via arterial cannula 16, which may be inserted in the ascending aorta or the femoral artery. NO-containing gas may be introduced into the CBP circuit via NO delivery device 18 which is and in fluid communication with NO generating device/NO reservoir 17 and with CBP system 20 downstream of oxygenator 13. NO-containing gas may be introduced into the CBP circuit at any point after oxygenator 13 for return to the arterial circulation. In the CBP circuit illustrated in FIG. 1, this includes introduction between oxygenator 13 and filter 15 (as shown) or between filter 15 and arterial cannula 16 (not shown). Alternatively, NO-containing gas may be introduced into the CBP circuit in oxygenator 13, provided blood is oxygenated prior to contact with the NO-containing gas within oxygenator 13.

In a further aspect, the invention provides extracorporeal oxygenation systems which comprise a component for introduction of NO-containing gas into oxygenated (arterialized) blood prior to infusion into the body of a patient. Such structure of such apparati are generally as described above, with the addition of a device for introduction of NO-containing gas into the portion of the circuit which contains arterialized blood. The device for introduction of NO-containing gas into oxygenated blood prior to infusion may comprise a container, gas cylinder or receptacle for holding or locally generating the NO-containing gas, referred to as an "NO generator/receptacle". The device for introduction of the NO-containing gas into the arterialized blood will typically include a pump, injector or metering device to facilitate delivery of the NO-containing gas into the oxygenated blood of the extracorporeal circuit for return to the patient, referred to as an "NO delivery device".

Extracorporeal oxygenation systems are simplified CBP circuits which provide cardiac and respiratory support oxygen to patients. In these systems venous blood is withdrawn from the patient, oxygenated outside of the body, and returned either via the arterial system or the venous system. A typical extracorporeal oxygenation system uses a membrane oxygenator and is referred to as an extracorporeal membrane oxygenation (ECMO) system. The system comprises a venous cannula typically placed in the right common femoral vein for extraction and an arterial cannula placed either into the right femoral artery (veno-arterial ECMO) or the right internal jugular vein (veno-venous ECMO) for infusion. In the methods of the invention, to obtain direct administration of NO-containing gas into arterialized blood, the NO-containing gas is introduced into the withdrawn blood at any point between the oxygenator and the venous or arterial infusion cannula. Alternatively, NO-containing gas may be introduced into the withdrawn blood in the oxygenator, provided blood is oxygenated prior to contact with the NO-containing gas within the oxygenator.

In a particular embodiment, the NO-containing gas is administered via a device, for example an ECMO device. The NO-containing gas may be administered within the oxygenation compartment of the device, wherein the oxygenation compartment contains two components. The first component is a first gas exchange membrane (also referred to as a membrane oxygenator) which exchanges oxygen for $CO_2$ in blood to produce arterialized blood. The second component is a second gas exchange membrane which exchanges NO for $O_2$ in the arterialized blood. The first and second components can be either structurally separate components in fluid communication or combined as one structure containing separate reaction areas within the oxygenation compartment. In either case, the second component is down-stream of the first component, as defined by the direction of blood flow in the device. Thus, NO-containing gas is administered either into the oxygenation compartment after $O_2$ has been administered into the oxygenation compartment and after $CO_2$ has been released, or NO is administered downstream of the oxygenation compartment (after blood has left the oxygenator but before it is delivered back into the patient) or both.

Figure 2:
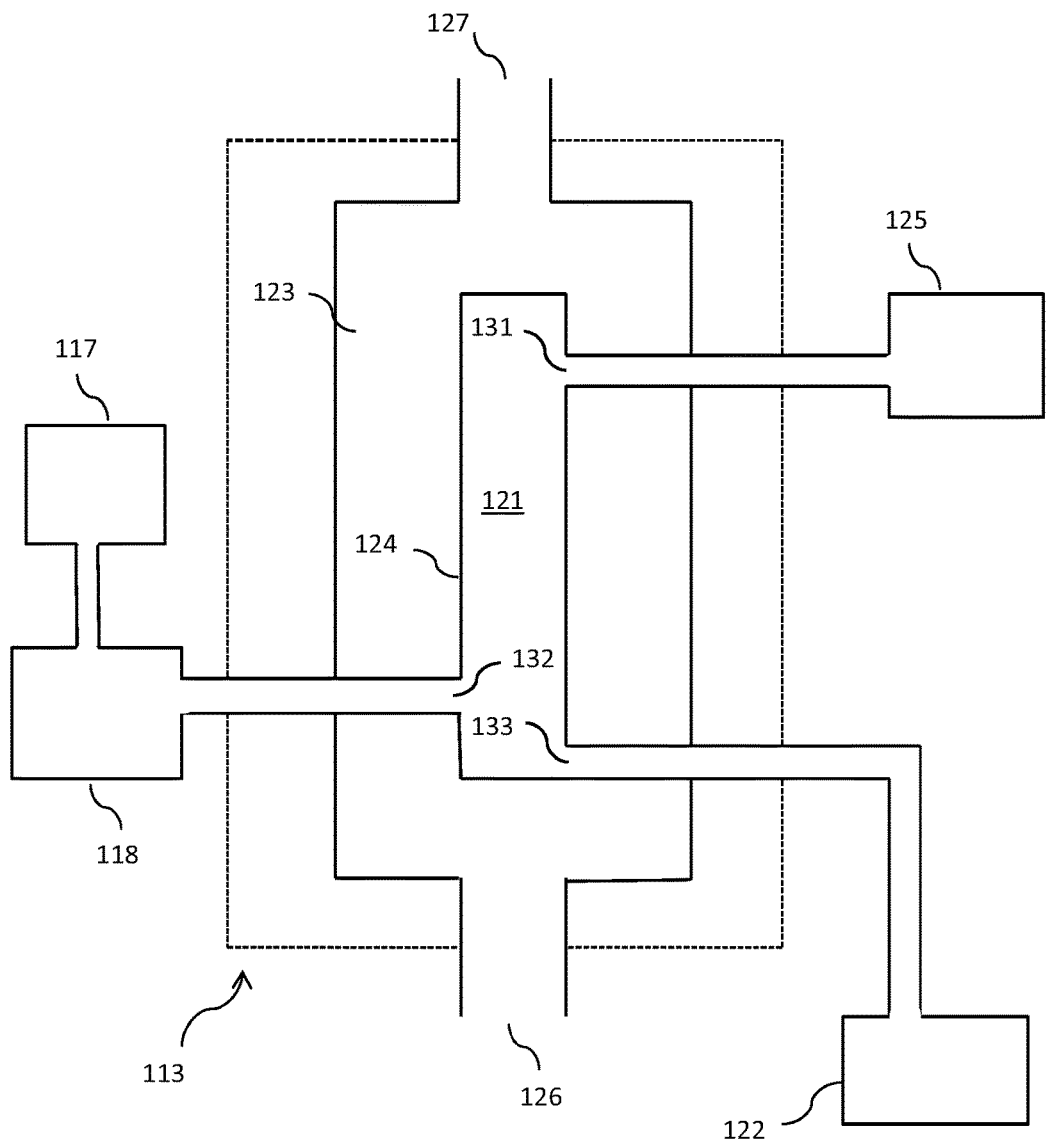
FIG. 2 illustrates a first embodiment of the oxygenation compartment of an ECMO device.

FIG. 2 illustrates oxygenation compartment 113 of an ECMO device, wherein oxygenation of blood and delivery of NO both occur within gas transfer unit 121. In this embodiment, blood enters oxygenation compartment 113 through inlet 127, flows into chamber 123, and exits oxygenation compartment 113 through outlet 126. Chamber 123 is in contact with gas permeable membrane 124 of gas transfer unit 121. Oxygen source 125 is also in fluid communication with gas transfer unit 121 through inlet 131. As blood enters the upstream portion of chamber 123, oxygen introduced into gas transfer unit 121 from oxygen source 125 diffuses through gas permeable membrane 124 into the blood, exchanging oxygen for $CO_2$. The portion of gas transfer unit 121 downstream of inlet 131 is in fluid communication with NO delivery device 118, through inlet 132. NO delivery device 118 is in fluid communication with NO generator/reservoir 117 to deliver NO to gas transfer unit 121. As the oxygenated blood in chamber 123 comes into contact with gas permeable membrane 124 downstream of inlet 131, NO introduced into gas transfer unit 121 through inlet 132 diffuses through gas permeable membrane 124 into the oxygenated blood, exchanging NO for oxygen. After delivery of oxygen and NO to the blood, remaining oxygen and NO may be removed from gas transfer unit 121 to venting device 122 via outlet 133 in fluid communication with gas transfer unit 121.

Figure 3:
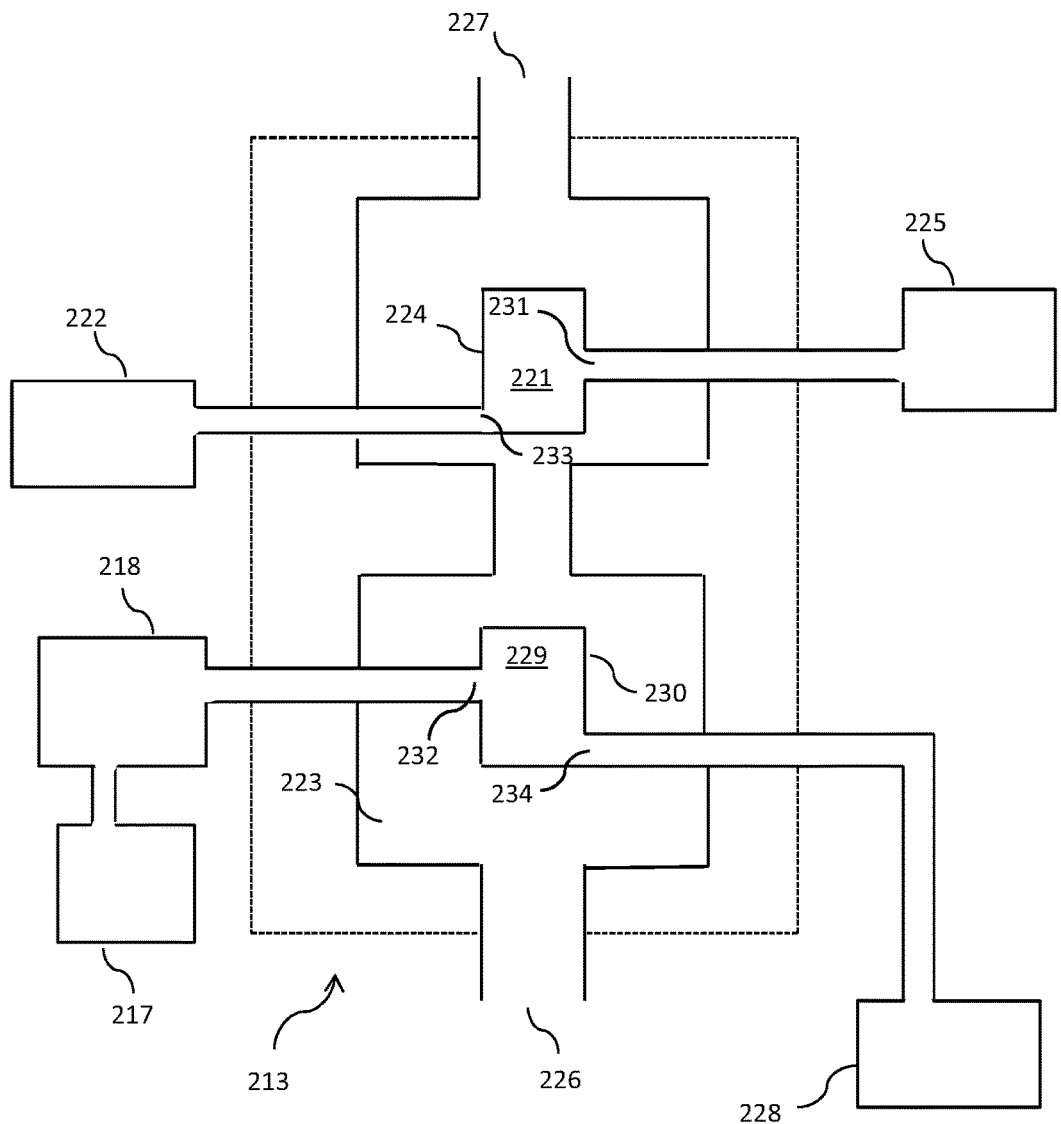
FIG. 3 illustrates an alternative embodiment of the oxygenation compartment of an ECMO device.

FIG. 3 illustrates oxygenation compartment 113 of an ECMO device, wherein oxygenation of blood and delivery of NO occur within structurally separate components 221 and 229 of oxygenation compartment 213. In this embodiment, blood enters oxygenation compartment 213 through inlet 227, flows into chamber 223, and exits oxygenation compartment 213 through outlet 226. Chamber 223 is in contact with oxygen permeable membrane 224 of oxygen transfer unit 221. Oxygen source 225 is also in fluid communication with oxygen transfer unit 221 through inlet 231. As blood enters the upstream portion of chamber 223, oxygen introduced into oxygen transfer unit 221 from oxygen source 225 diffuses through oxygen permeable membrane 224 into the blood, exchanging oxygen for $CO_2$.

Downstream of inlet 231, remaining oxygen may be removed from oxygen transfer unit 221 to oxygen venting device 222 via outlet 233 in fluid communication with oxygen transfer unit 221. The downstream portion of chamber 223 is in contact with NO permeable membrane 230 of NO transfer unit 229. NO delivery device 218 is also in fluid communication with NO transfer unit 229 through inlet 232. NO delivery device 218 is in fluid communication with NO generator/reservoir 217 to deliver NO to NO chamber 229. As oxygenated blood flows to the downstream portion of chamber 223, it comes into contact with NO permeable membrane 230 of NO transfer unit 229, and NO introduced into NO transfer unit 229 through inlet 232 diffuses into the oxygenated blood, exchanging NO for oxygen. After delivery of NO to the blood, remaining NO may be removed from NO transfer unit 229 to NO venting device 228 via outlet 234 in fluid communication with NO transfer unit 229.

Figure 4:
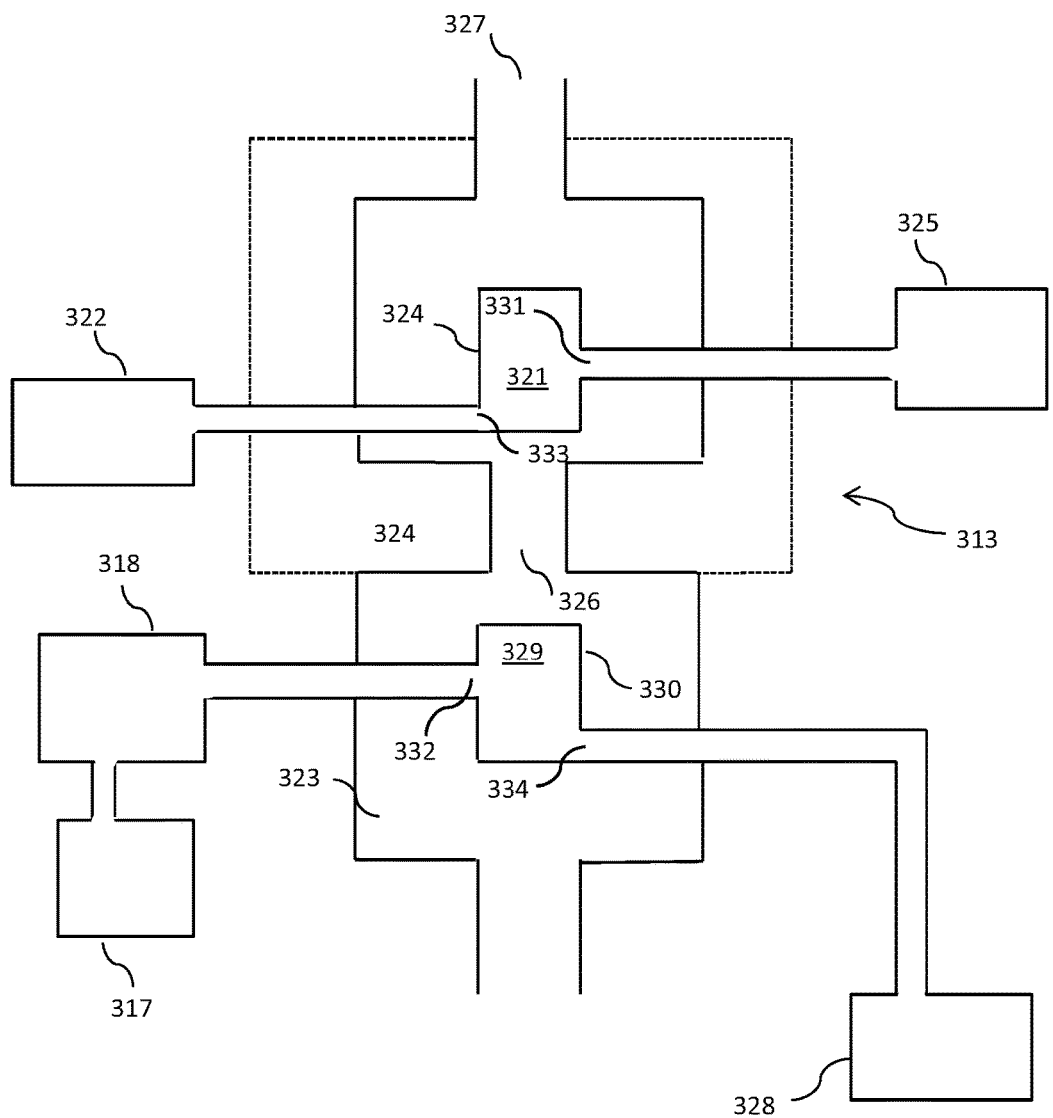
FIG. 4 illustrates a further alternative embodiment of the oxygenation compartment and NO delivery system of an ECMO device.

FIG. 4 illustrates oxygenation compartment 313 of an ECMO device, wherein oxygenation of blood occurs within oxygenation compartment 313 and delivery of NO to the blood occurs downstream of and outside oxygenation compartment 313. In this embodiment, blood enters oxygenation compartment 313 through inlet 327, flows into chamber 323, and exits oxygenation compartment 313 through outlet 326. Chamber 323 is in contact with oxygen permeable membrane 324 of oxygen transfer unit 321 within oxygenation compartment 313. Oxygen source 325 is also in fluid communication with oxygen transfer unit 321 through inlet 331. As blood enters the upstream portion of chamber 323, oxygen introduced into oxygen transfer unit 321 from oxygen source 325 diffuses through oxygen permeable membrane 324 into the blood, exchanging oxygen for $CO_2$. Downstream of inlet 331, remaining oxygen may be removed from oxygen transfer unit 321 to oxygen venting device 322 via outlet 333 in fluid communication with oxygen transfer unit 321. The downstream portion of chamber 323 is in contact with NO permeable membrane 330 of NO transfer unit 329, which is outside oxygenation compartment 313. NO delivery device 318 is also in fluid communication with NO transfer unit 329 through inlet 332. NO delivery device 318 is in fluid communication with NO generator/reservoir 317 to deliver NO to NO chamber 329. As oxygenated blood exits oxygenation compartment 313 and flows to the downstream portion of chamber 323, it comes into contact with NO permeable membrane 330 of NO transfer unit 329, and NO introduced into chamber 329 through inlet 332 diffuses into the oxygenated blood, exchanging NO for oxygen. After delivery of NO to the blood, remaining NO may be removed from NO transfer unit 329 to NO venting device 328 via outlet 334 in fluid communication with NO transfer unit 329.

The NO-containing gas may be administered in the oxygenator after the blood has been partially oxygenated or fully oxygenated and may be administered separately from the addition of the oxygen. The NO-containing gas is typically administered after $O_2$ administration and $CO_2$ release.

In various embodiments, methods of the present invention include delivery of NO-containing gas directly into arterial blood by injection, catheterization, infusion, or continuous infusion into an artery, for example, a central or peripheral artery (e.g., the aorta, femoral, brachial, radial, ulnar, dorsalis pedis, etc.).

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of treating, preventing or inhibiting ischemia or hypoxia in a patient comprising
    a) oxygenating withdrawn blood of the patient through a gas exchange membrane at a first reaction area of a gas transfer unit within an oxygenation compartment of an extracorporeal membrane oxygenation system (ECMO) to produce arterialized blood;
    b) after oxygenation, delivering a therapeutically effective amount of nitric oxide-containing gas directly into the arterialized blood of the patient through the gas exchange membrane at a second reaction area of the gas transfer unit downstream of the first reaction area; and
    c) infusing the blood produced in step b) into the patient via an arterial cannula,
    wherein any remaining oxygen and nitric oxide (NO) is removed from the gas transfer unit through an outlet in the gas transfer unit downstream of the second reaction area.

2. The method of claim 1, wherein delivery of the nitric-oxide containing gas into the arterialized blood is bolus delivery of the nitric oxide-containing gas.

3. The method of claim 1, wherein a delivery concentration of nitric oxide-containing gas is in the range of 0.1-500 ppm.

4. The method of claim 1 wherein delivery of the nitric oxide containing gas into the arterialized blood is by continuous administration into the arterialized blood.

5. The method of claim 1 wherein the blood produced in step (b) is infused into the patient before onset of the ischemia or hypoxia.

6. The method of claim 1 wherein the blood produced in step (b) is infused into the patient after onset of the ischemia or hypoxia.

7. The method of claim 1 further comprising:
    introducing the oxygen into the gas transfer unit from an oxygen source in fluid communication with the gas transfer unit through a first inlet in the gas transfer unit; and
    introducing the NO into the gas transfer unit from a NO delivery device in fluid communication with the gas transfer unit through a second inlet in the gas transfer unit downstream of the first inlet.

8. The method of claim 7 further comprising generating and/or storing NO in a NO generator/reservoir connected to the NO delivery device.

9. The method of claim 1 further comprising venting the remaining oxygen and NO with a venting device in fluid communication with the gas transfer unit through an outlet of the gas transfer unit.

10. An extracorporeal membrane oxygenation (ECMO) system comprising:
an oxygenation compartment comprising:
a chamber, wherein blood enters the oxygenation compartment though the chamber; and
a gas transfer unit having a first reaction area, a second reaction area downstream of the first reaction area, and an outlet downstream of the second reaction area, and
wherein the gas transfer unit is separated from the chamber by a gas exchange membrane which exchanges oxygen for carbon dioxide in the blood to produce arterialized blood in the first reaction area of the gas transfer unit, and exchanges nitric oxide (NO) for oxygen in the arterialized blood in the second reaction area of the gas transfer unit, and
a venting device in fluid communication with the gas transfer unit through the outlet of the gas transfer unit operable to receive any remaining oxygen and NO.

11. The ECMO system of claim 10 further comprising:
an oxygen source in fluid communication with the gas transfer unit through a first inlet in the gas transfer unit; and
a NO delivery device in fluid communication with the gas transfer unit through a second inlet in the gas transfer unit downstream of the first inlet.

12. The ECMO system of claim 11 further comprising a NO generator/reservoir connected to the NO delivery device for generating and/or holding the NO.

* * * * *